United States Patent [19]

Cattani

[11] 4,293,300

[45] Oct. 6, 1981

[54] LIQUID SEPARATING AND EVACUATING DEVICE FOR FLUID SUCTION EQUIPMENT

[75] Inventor: Augusto Cattani, Parma, Italy

[73] Assignee: Officine Augusto Cattani & C. S.A.S., Parma, Italy

[21] Appl. No.: 109,200

[22] Filed: Dec. 31, 1979

[30] Foreign Application Priority Data

Jan. 15, 1979 [IT] Italy .................................. 4005 A/79

[51] Int. Cl.³ ............................................ A61C 17/04
[52] U.S. Cl. ....................................... 433/92; 137/205
[58] Field of Search ................... 433/92; 55/189, 219; 251/211; 15/353; 137/205

[56] References Cited

U.S. PATENT DOCUMENTS

| | | | |
|---|---|---|---|
| 1,484,505 | 2/1924 | Kiefer | 137/205 |
| 1,661,608 | 3/1928 | Grauel | 137/205 |
| 2,406,214 | 8/1946 | Garnier | 55/219 |
| 3,002,523 | 10/1961 | Rabbitts | 137/205 |
| 3,078,579 | 2/1963 | Jones et al. | 433/92 |
| 3,355,862 | 12/1967 | Blanchet et al. | 55/219 |
| 3,657,819 | 4/1972 | Söderqvist | 433/92 |
| 3,847,573 | 11/1974 | Gandrud | 433/92 |
| 3,901,670 | 8/1975 | Minami | 55/219 |

FOREIGN PATENT DOCUMENTS 1383801 2/1975 United Kingdom .................. 433/92

*Primary Examiner*—Gene Mancene
*Assistant Examiner*—John J. Wilson
*Attorney, Agent, or Firm*—Mason, Fenwick & Lawrence

[57] ABSTRACT

Disclosed herein is a liquid separating and evacuating device for fluid suction equipment and, in particular, for dental surgery equipment, with which it is possible to separate the air from the liquids and to continuously drain the latter without interrupting the suction.

The said device consists essentially of a cylindrical container, placed on a vertical axis, that is provided on the bottom part thereof with a draining valve. Placed inside the said container there is a horizontal partition that is divided into two superposed chambers. This partition has a valve which either allows or prevents the liquid from passing from the first chamber to the second chamber.

A float contained in the first chamber controls, by actuating a pneumatic distributor, the opening and the closing of the aforementioned valves which successively allow the liquid to pass from the first chamber to the second chamber and from the latter to the outside.

3 Claims, 4 Drawing Figures

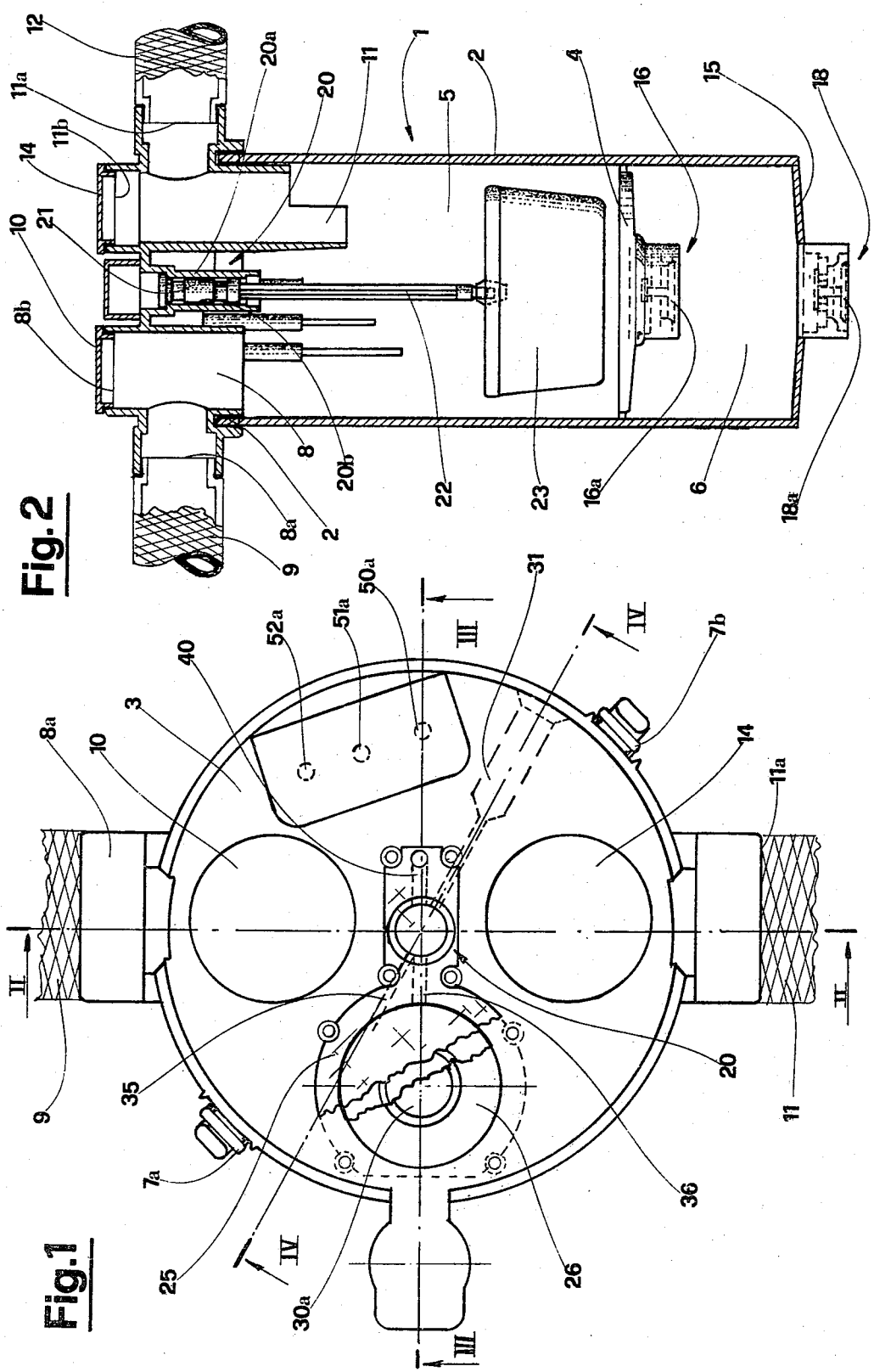

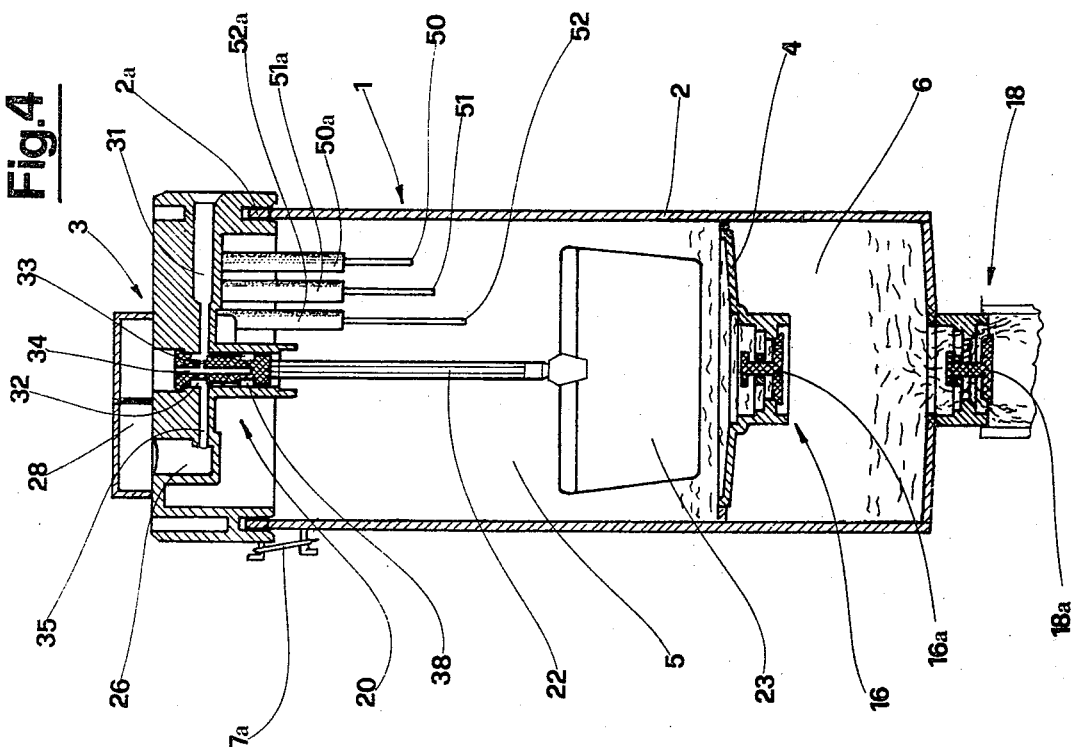
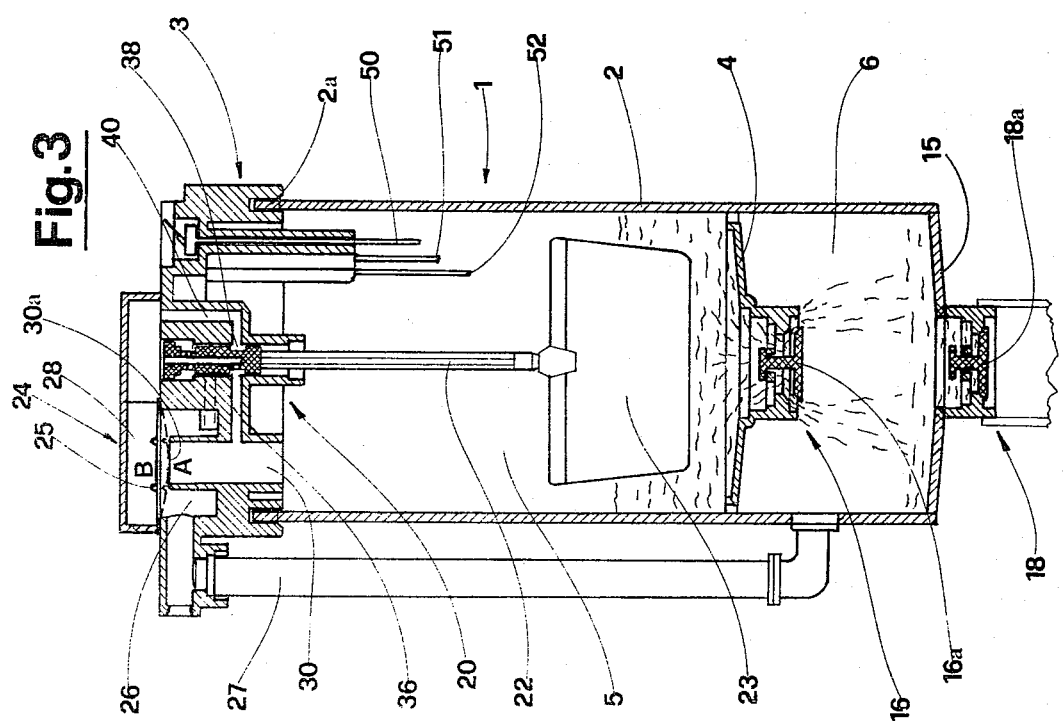

LIQUID SEPARATING AND EVACUATING DEVICE FOR FLUID SUCTION EQUIPMENT

BACKGROUND OF THE INVENTION

The invention has as its subject a liquid separating and evacuating device for fluid suction equipment and, in particular, for dental surgery equipment.

DESCRIPTION OF THE PRIOR ART

During treatment given inside the mouth, dental treatment for example, it is impossible for the patient to swallow the saliva produced by the salivary glands located in the mouth itself. Furthermore, while the said treatment is taking place the flow of blood and the use of various liquid substances is frequent, and the said liquids have to be evacuated along with the saliva.

For this purpose a probe connected to a suction pump is inserted in the mouth of the patient, the latter attending to the evacuation of the liquids held inside the mouth itself.

The fluid extracted, normally consisting of air, saliva, blood and various liquids, depending upon the type of treatment being given, can be made to pass thru the pump and to be discharged externally. To do this, however, can jeopardize the satisfactory operation and the life span of the pump since the liquids present in the fluid are corrosive and the cause of encrustment.

In order to overcome this particular problem a device can be inserted in the suction tube, between the pump and the probe, which separates the liquids from the air and looks after the discharging externally of the said liquids.

Centrifugal separating devices exist at the present time, and these virtually consist of a container into which the sucked fluid enters in a tangential direction. In this way the liquids adopt a vortical downward motion and are discharged in a continuous fashion from below.

The said devices are provided with a float which, with the aid of suitable contrivances, interrupts the suction of the pump at the time the liquid inside the container reaches too high a level, and when this occurs the liquid is discharged by gravity. When the level of the liquid drops, the float sets the suction pump back in motion, and the vortex of the liquid is re-created.

One problem with this type of separating device is that it requires a motor of high power to be used for the suction pump in order to enable the suction circuit to operate properly.

Another problem is that the suction pump is constantly and rapidly switched on and off when the quantity of liquid arriving is high.

SUMMARY OF THE INVENTION

One object of the invention is to overcome the aforementioned difficulties by making available a separating and evacuating device which does not require a motor of high power to be used for the suction pump and which, during operation, does not constantly and rapidly switch the said pump on and off, though it does allow a large quantity of liquid to be separated and evacuated.

Another object of the invention is to make available a separating and evacuating device that is highly reliable yet simple from the operating viewpoint.

These and other objects too are attained with the device in question, essential features of which are that it comprises: a first chamber into which the fluid extracted arrives, this being designed to effect the separation from the air of the liquid part of the fluid extracted, kept, during the operation of the device, at a pressure less than that of the atmosphere; a second chamber placed beneath the said first chamber; automatic means, tripped by the level of the liquid present in the first chamber, designed to alternately create in the said second chamber a pressure approximately identical to that of the atmosphere when the level of the liquid in the first chamber is lower than a pre-set value, and a pressure approximately identical to that of the first chamber when the level of the liquid in the first chamber is above the said pre-set value; and valve means designed to alternately allow and prevent liquid from passing from the said first chamber to the said second chamber, and to alternately allow and prevent liquid from passing from the said second chamber to the outside, the passing of the liquid from the first to the second chamber being allowed when the two chambers are at approximately the same pressure and being prevented when the pressure of the second chamber is approximately identical to that of the atmosphere, the passing of the liquid from the second chamber to the outside being allowed when the pressure of the second chamber is approximately identical to that of the atmosphere and being prevented when the pressure of the second chamber is approximately identical to that of the first chamber.

BRIEF DESCRIPTION OF THE DRAWINGS

Further characteristics and advantages of the invention will emerge more obviously from the detailed description that follows of one preferred but not sole form of embodiment for the device in question, illustrated purely as an unlimited example on the accompanying drawings, in which:

FIG. 1 shows, in a view seen from above, the device forming the subject of the invention, with certain parts removed in order that others may be seen more clearly;

FIG. 2 shows, in a reduced scale, a section of the device along the plane followed by the line II—II in FIG. 1;

FIG. 3 shows, in a reduced scale, a section of the device along the plane followed by the line III—III in FIG. 1;

FIG. 4 shows, in a reduced scale, a section of the device along the plane followed by the line IV—IV in FIG. 1.

DESCRIPTION OF THE PREFERRED EMBODIMENT

The separating and evacuating device (1) in question is virtually constituted by a cylindrical container (2) placed on a vertical axis, the upper edge (2a) of which is hermetically connected, thru two elastic rings (7a) and (7b), to a covering member (3). The container (2) is divided, by means of a partition (4) positioned in a substantially horizontal fashion, into two areas that constitute a first chamber (5) and a second chamber (6) placed beneath the said first chamber (5).

The first chamber (5) communicates directly with a suction pipe (8), machined in the covering member (3), which is in turn connected, thru a first flexible tube (9), one extremity of which is visible in the drawing, to a suction pump that is not illustrated. During operation, the first chamber (5) is maintained, thru the said suction pump, at a pressure below that of the atmosphere. The suction pipe (8) has two extremities, (8a) and (8b), respectively, to each of which it is possible, depending on the space available for the installation of the device (1), to connect the flexible tube (9). In the example illustrated, the tube (9) is connected to the extremity (8a), while the extremity (8b) is sealed by a first cover (10). The first chamber (5) communicates directly with an inlet pipe (11), machined in the covering member (3) which, in turn, is connected, thru a second flexible tube (12), one extremity of which is visible in the drawing, to one or more suction probes that extract fluid from the mouth of the patient. When the device is in operation, the fluid extracted, deprived of any solid bodies thru the use of a non-illustrated filter placed in the inlet pipe (11), passes into the first chamber (5) wherein the separation of the liquids from the air takes place, and the former drop downwards towards the bottom of the said chamber. The inlet pipe (11) has two extremities, (11a) and (11b), respectively, to each of which it is possible, depending on the space available for the installation of the device (1), to connect the flexible tube (12). In the example illustrated, the tube (12) is connected to the extremity (11a), while the extremity (11b) is sealed by a second cover (14).

In order to prevent part of the liquid from being drawn by the pump thru the suction pipe (8), both this and the inlet pipe (11) are so arranged as to not face each other. Provision is made in the partition (4) and in a bottom wall (15) with which the container (2) is provided, for a first mushroom valve (16) and a second mushroom valve (18), respectively, which constitute valve means for alternately allowing and preventing the liquid from passing from the first chamber (5) to the second chamber (6), thru the valve (16), and the liquid from passing from the second chamber (6) to the outside, thru the valve (18).

The valves (16) and (18) are arranged in such a way that their opening takes place thru a downward movement of the obturation means (16a) and (18a), respectively. In this way liquids are allowed to pass from the first to the second chamber when chambers (5) and (6) are at approximately the same pressure since the obturation means (16a) of the valve (16) drop by gravity and open the passage but are prevented from doing this when the chamber (6) is at a pressure approximately identical to that of the atmosphere since the said difference in pressure existing between the two chambers (as stated, the first chamber (5) is, during operation, always at a pressure below that of the atmosphere) pushes the obturation means (16a) of the valve (16) upwards against the set of the valve until the passage for the liquid is closed. Likewise the valve (18) allows the liquid to pass from the second chamber (6) to the outside when the chamber (6) is at a pressure approximately identical to that of the atmosphere, and prevents the said passing of the liquid when the chamber (6) is under vacuum with respect to the outside (particularly when the chamber (6) is at an almost identical pressure to that of the chamber (5)).

The device (1) comprises automatic means, tripped by the level of the liquid present in the first chamber (5), designed to alternately create in the said second chamber (6) either a pressure approximately identical to that of the atmosphere, when the level of the liquid in the first chamber (5) is below a pre-set value, or a pressure identical approximately to that of the first chamber (5), when the level of the liquid in the latter is above the pre-set value.

The said automatic means comprise a pneumatic distributor (20) whose body is machined in the covering member (3). In the cylindrical cavity (20b) inside the body (20a) of the distributor, placed on a vertical axis and communicating directly with the first chamber (5), slides a cursor (21) connected integrally, on a vertical axis, to one extremity of a rigid rod (22) positioned vertically. The other extremity of the rod (22) is connected integrally to a float (23) contained in the first chamber (5).

The said float (23) is designed to pass to the automatic means an operating signal determined by the level of the liquid present in the first chamber (5). Depending on the position adopted by the float (23), the cursor (21) slides in the cavity (20b) of the distributor (20) and either opens or closes the paths of the said distributor.

Furthermore, the automatic means comprise a pneumatic valve (24) whose obturation means are constituted by a diaphragm (25) actuated by the distributor (20). The said valve (24) is constituted by a lower annular cavity (26) placed on a vertical axis and communicating directly, via an external channel (27), with the second chamber (6) and alternatively either with the outside or with the first chamber (5), and by an upper cavity (28) placed in communication, via the channels described hereinafter, with the annular cavity (26), on a horizontal contact plane, with the interposition of the diaphragm (25), the non-operative position of which defines the horizontal contact plane. In its central area the annular cavity (26) is provided with a coaxial hole (30), the upper extremity (30a) of which is at an elevation slightly less than that of the said contact plane and communicates directly with the first chamber (5).

The pneumatic distributor (20) and the pneumatic valve (24), operated by the level of the liquid present in the first chamber (5) thru the float (20), alternately place the second chamber (6) either in communication with the first chamber (5) or with the outside.

When, in fact, the level of the liquid present in the first chamber (5) is not sufficient to cause the flotation of the float (23) (FIG. 4), the upper cavity (28) of the pneumatic valve (24) is placed in communication with the outside via a first passage constituted by a channel (31) machined in the covering member (3), the extremities of which communicate with the outside and with the cylindrical cavity (20b) of the pneumatic distributor, respectively, by a first groove (32) machined circumferentially in the cursor (21), and by the channels (33) and (34) machined in the inside of the cursor (21). The diaphragm (25) is thrust, by the difference in pressure existing between the upper cavity (28) and the hole (30) in the pneumatic valve, to close the extremity (30a) of the hole (30) (position A shown with dashes in FIG. 3). The annular cavity (26) is placed in communication with the outside via a second passage constituted by a channel (31), by the first groove (32) and by a channel (35) machined in the covering member (3), the extremities of which communicate with the cylindrical cavity (20b) of the pneumatic distributor and with the annular cavity (26) of the pneumatic valve. In this way the second chamber (6) connected, as stated, to the annular cavity (26) is in communication with the outside and is thus at an approximately atmospheric pressure.

When the level of the liquid present in the first chamber (5) is sufficient to cause the flotation of the float (23) (FIG. 3), the cursor (21) is displaced upwards and it closes the first passage and the second passage. The upper cavity (28) of the pneumatic valve (24) is placed in communication with the first chamber (5) and is thus carried to a pressure less than that of the atmosphere via a third passage constituted by the channel (36) machined in the covering member (3), the extremities of which communicate with the hole (30) in the pneumatic valve and with the cylindrical cavity (20b) of the pneumatic distributor, respectively, by a second groove (38) machined circumferentially in the cursor (21) in a position underneath the first groove (32), and by a channel (40) machined in the covering member (3), the extremities of which communicate with the cylindrical cavity (20b) and with the upper cavity (28), respectively.- Because of the vacuum existing in the cavity (28), the diaphragm (25) rises from the extremity (30a) of the hole (30), position B in FIG. 3, and allows there to be a communication between the first chamber (5) and the annular cavity (26) and thus between the first chamber (5) and the second chamber (6) which, in this way, is at a pressure approximately identical to that existing in the first chamber.

In order to stop the operation of the suction pump in the event of the fluid extracted containing a greater quantity of liquid that can be evacuated by the device (1), three level measuring contrivances, (50), (51), and (52), respectively, are inserted in the first chamber (5), placed at different heights. This insertion of level measuring contrivances in the chamber (5) is allowed by the tubes (50a), (51a) and (52a), respectively, which are machined in the covering member (3) and place the upper part of this in direct communication with the first chamber (5).

The level measuring contrivances (50), (51) and (52) supply an electric signal when their lower extremity is immersed in the liquid and are so connected electrically as to interrupt the operation of the suction pump when all three have their extremity immersed in the liquid, and to put the pump back in operation when the level of the liquid drops below that of the measuring contrivance (51). In this way it is possible to avoid the motor that operates the suction pump being switched on and off in rapid succession.

The operation of the device in question takes place in the following way: When the suction pump is operated, the first chamber (5) is carried to a pressure below that of the atmosphere. Fluid that enters the first chamber (5) is extracted thru one or more suction probes. Until the level of the liquid allows the flotation of the float (23) the second chamber (6) is, as stated, at atmospheric pressure and thus the valve (16) prevents the liquid from passing from the first to the second chamber and, naturally, air from passing from the second to the first chamber. When the level of the liquid in the chamber (5) is such as to allow the flotation of the float (23), the latter moves upwards (FIG. 3) and places the first chamber (5) in communication, as stated, with the second chamber (6). The valve (16), subject to almost identical pressure both at the top and at the bottom, opens and allows the liquid to pass from the first to the second chamber. Contemporaneously, the valve (18), subjected at the bottom to atmospheric pressure closes and prevents the liquid from passing from the second chamber (6) to the outside and also prevents the air from entering the second chamber (6). When the level of the liquid in the first chamber (5) drops below a value whereby the flotation of the float (23) is no longer possible, the latter returns downwards to the position shown in FIG. 4, the valve (16) closes again and the valve (18) opens again to thus allow the liquid present in the second chamber (6) to be evacuated externally.

Should the quantity of liquid extracted by the suction probe exceed the quantity that can be evacuated, the chamber (5) fills with liquid.

Once the level of the liquid reaches the third measuring contrivance (50), the operation of the suction pump is interrupted and the chambers (5) and (6) reach the atmospheric pressure. The valves (16) and (18) open and discharge the liquid continuously by gravity. The suction pump resumes its operation once the level of the liquid in the chamber (5) arrives at a lower level than that of the intermediate measuring contrivance (51).

The invention can undergo numerous modifications of a practical nature without in any way deviating from the conceptual framework of the invention as per the claims listed hereinafter.

What is claimed is

1. A liquid separating and evacuating device for dental surgery fluid suction equipment comprising a first chamber connected to a vacuum source, a fluid inlet pipe connected to the first chamber for directing fluid into the first chamber which is kept at sub-atmospheric pressure during the operation of the device, a second chamber positioned beneath said first chamber, automatic means responsive to the level of liquid present in the first chamber for causing the second chamber to be vented to atmosphere so as to be at a pressure approximately identical to that of the atmosphere in response to the level of the liquid in the first chamber being lower than a pre-set value and for causing the second chamber to communicate with the first chamber so as to be at sub-atmospheric pressure approximately identical to that of the first chamber in response to the level of liquid in the first chamber being above said pre-set value, first valve means for preventing liquid from passing from the first chamber to the second chamber in response to the second chamber being at a higher pressure than the first chamber and for permitting liquid flow from the first chamber to the second chamber when the pressure in the first chamber is approximately the same as pressure in the second chamber and second valve means for allowing liquid to be discharged from the second chamber to the outside in response to pressure inside the second chamber being approximately equal to atmospheric pressure and for precluding such discharge when pressure in the second chamber is less than atmospheric pressure, wherein said automatic means includes a pneumatic distributor and a pneumatic valve including a diaphragm actuated by the said pneumatic distributor, said diaphragm being movable between a first position in which said second chamber is placed in communication with the first chamber and a second position in which said second chamber is placed in communication with the outside, a float contained in said first chamber, a rigid vertical rod having upper and lower ends and connected on its lower end to said float for vertical movement therewith and a movable valve spool connected to the upper end of said rod for movement in said pneumatic distributor in accordance with the liquid level in said first chamber.

2. A liquid separating and evacuating device according to claim 1 wherein said first and second chambers are formed in a hollow cylindrical container having a vertical axis and including a substantially horizontal partition dividing said container into two first and second chambers, said first valve means being mounted in said partition and said container further including a bottom wall in which said second valve means is mounted, said first and second valve means each comprising a mushroom valve having a movable valving element movable downwardly to an open condition and further including a cover member connected hermetically to the upper end of said cylindrical container.

3. A liquid separating and evacuating device according to claim 2 wherein said cover member includes an upper cavity above said diaphragm, said pneumatic distributor, which is formed in said cover member, and an internal cylindrical cavity having a vertical axis and communicating directly at its lower end with the said first chamber and at its upper end with said upper cavity, said movable valve spool being mounted in said internal cylindrical cavity, said pneumatic valve including a lower annular cavity that communicates directly with the second chamber and alternately with either the outside or the said first chamber, wherein the upper end of said annular cavity is covered by and supports said diaphragm, the lower annular cavity having a conduit in the central area thereof having a lower end opening into the first chamber and an upper coaxial opening which is at a level slightly lower than that of said contact plane and communicating directly with said first chamber when said diaphragm is in its first position but being closed by said diaphragm when said diaphragm is in its second position.

* * * * *